United States Patent [19]
Riedel et al.

[11] Patent Number: 5,763,637
[45] Date of Patent: Jun. 9, 1998

[54] PROCESS FOR PREPARING DIMETHYL VINYLPHOSPHONATE FROM DIMETHYL 2-ACETOXYETHANEPHOSPHONATE

[75] Inventors: Knut Riedel, Hofheim; Udo Dettmeier; Guenter Roscher, both of Kelkheim, all of Germany

[73] Assignee: Hoechst Aktiengesellschaft, Frankfurt, Germany

[21] Appl. No.: 587,645

[22] Filed: Jan. 17, 1996

[30] Foreign Application Priority Data

Jan. 18, 1995 [DE] Germany ............ 195 01 336.0

[51] Int. Cl.⁶ .................................... C07F 9/40
[52] U.S. Cl. ...................................... 558/142
[58] Field of Search ............................. 558/142

[56] References Cited

U.S. PATENT DOCUMENTS 4,388,252  6/1983  Dürsch et al. .
4,894,470  1/1990  Roscher et al. .
5,132,444  7/1992  Northemann et al. ............ 558/142 X

FOREIGN PATENT DOCUMENTS 0032663  7/1981  European Pat. Off. .
0281122  9/1988  European Pat. Off. .

OTHER PUBLICATIONS

Chemical Abstracts, vol. 078, No. 5, p. 517, Feb. 5, 1973, Columbus, Ohio, U.S., abstract No. 029900, Yamagami M et al: "Induced addition of dialkyl phosphites to olefins and pyrolysis of the 1:1 adducts".

Primary Examiner—Michael G. Ambrose
Attorney, Agent, or Firm—Connolly and Hutz

[57] ABSTRACT

The invention relates to a process for preparing dimethyl vinylphosphonate by thermal dissociation of dimethyl 2-acetoxyethanephosphonate in the gas phase, which comprises vaporizing dimethyl 2-acetoxyethanephosphonate and dissociating it without catalysis at a temperature of from 400° to 700° C. into dimethyl vinylphosphonate and acetic acid.

10 Claims, No Drawings

PROCESS FOR PREPARING DIMETHYL VINYLPHOSPHONATE FROM DIMETHYL 2-ACETOXYETHANEPHOSPHONATE

The invention relates to a process for preparing dimethyl vinylphosphonate from dimethyl 2-acetoxyethanephosphonate.

Dialkyl vinylphosphonates are important as precursors for preparing pure vinylphosphonic acid and as monomers in copolymerization for the production of adhesives or flame-resistant plastics. The preparation of vinylphosphonic acid derivatives from the corresponding 2-acetoxyethanephosphonic acid derivatives is known. M. Yamagami et al. have obtained dimethyl vinylphosphonate in a yield of 52% by elimination of acetic acid in the gas phase at 550° C. According to the process of DE-A 30 01 894, alkyl acetates are eliminated from dialkyl 2-acetoxyethanephosphonates by heating at from 150° to 270° C. in the presence of acidic or basic catalysts. The process gives vinylphosphonic acid derivatives in a yield of from 70 to 85%, but always forms mixtures of vinylphosphonic acid derivatives which contain varying amounts (at most 23%) of dialkyl vinylphosphonates in addition to monoalkyl vinylphosphonates and a number of other products.

In view of these unsatisfactory results, a switch was made in DE-A 31 20 437 to an improved two-stage process in which the alkyl acetate eliminated in the above-mentioned reaction was distilled off and the reaction product obtained in the distillation residue was subsequently reacted with ortho-esters of carbonic acid to give the desired dialkyl vinylphosphonates. EP 0 032 663 describes a process in which acetic acid elimination in the homogeneous liquid phase is accelerated by means of acid or basic catalysts. This process enables dialkyl vinylphosphonates to be prepared in a targeted manner and the use of the expensive ortho-esters to thus be avoided. However, the yield is only 80%. Furthermore, this process leaves something to be desired in terms of process technology because the process products have to be distilled off continually under reduced pressure, the space-time yields are relatively low and the catalyst liquid phase has to be regenerated after a time. The patent EP 0 456 049 A1 describes a process which is said to eliminate these disadvantages. In this process, the dialkyl 2-acetoxyethanephosphonates are passed in gaseous form over acidic or basic catalysts. However, this again gives a mixture of vinylphosphonic acid, monoalkyl ester and dialkyl ester which, owing to the strong tendency to polymerize, can be separated by distillation only with great difficulty, and, in particular, only very short catalyst operating lives can be achieved. After quite a short time, the reactor becomes blocked and has to be laboriously cleaned and recharged with catalyst.

There was therefore a need for a process which is industrially simple to carry out and allows dimethyl vinylphosphonate to be prepared with high selectivity and a high space-time yield.

This object is achieved by a process for preparing dimethyl vinylphosphonate by thermal dissociation of dimethyl 2-acetoxyethanephosphonate in the gas phase, which comprises vaporizing dimethyl 2-acetoxyethanephosphonate and dissociating it without catalysis at temperatures of from 400° to 700° C. into dimethyl vinylphosphonate and acetic acid. Preferably, the dissociation products are continuously removed from the reaction zone.

The starting compound dimethyl 2-acetoxyethanephosphonate can easily be obtained by reaction of dimethyl phosphite with vinyl acetate in the presence of peroxides (JACS 79, 1961–63, 1957). It is vaporized in a vaporizer and passed in gas form, possibly mixed with inert gas, through the reaction zone. The addition of from 1 to 100% by weight, preferably from 5 to 20% by weight, of methanol to the reaction mixture has been found to be particularly advantageous. The addition suppresses the formation of high-boiling by-products at temperatures above 600° C. The reaction zone can consist of an empty tube or a tube packed with an inert material, e.g. stainless steel packing, as is used for fractional distillation.

Vaporization can be carried out under reduced pressure and/or in a gas stream. A pressure range of from 5 to 500 mbar, in particular from 10 to 50 mbar, is favorable. A residence time of from 0.05 sec. to 20 sec., preferably 0.3 sec. to 3 sec., is set by means of the amount added and/or the gas flow. The temperature in the reaction zone is between 400° and 700° C., preferably between 550° and 650° C. It is also possible to work at a pressure above 500 mbar, with the difference between the total pressure and the partial pressure of the reaction components being produced by a gas which is inert under the reaction conditions. Inert gases which can be used are $N_2$, He, Ar, $CO_2$ or the vapor of lower hydrocarbons such as hexane, heptane or toluene.

The addition of methanol is particularly favorable. After leaving the reaction zone, the reaction mixture is cooled and analyzed.

The following examples illustrate the process of the present invention without restricting it to them.

EXAMPLE 1

In the vaporizer at 180° C., 104.5 g/h of dimethyl 2-acetoxyethanephosphonate are vaporized at 40 mbar. The vapor is passed, together with 15 l/h (s.t.p) of $N_2$, through a tube at 550° C. The residence time in the reactor is 0.5 sec. After condensation, a mixture of 13.2% of acetic acid, 30.6% of dimethyl vinylphosphonate and 55% of starting compound is obtained. The selectivity is 98%.

EXAMPLE 2

In the vaporizer at 180° C., 149 g/h of dimethyl 2-acetoxyethanephosphonate are vaporized at 30 mbar. The vapor is, together with 3.5 l/h (s.t.p.) of He, passed through a tube at 650° C. which is packed with Braunschweig VA coils. The residence time in the reactor is 0.45 sec. After condensation, a mixture of 28.8% of acetic acid, 68% of dimethyl vinylphosphonate and 0.1% of starting material is obtained. The selectivity is 98%.

EXAMPLE 3

In the vaporizer at 180° C., 80 g/h of dimethyl 2-acetoxyethanephosphonate are vaporized at 100 mbar. The vapor is, together with 2.5 l/h (s.t.p.) of $N_2$, passed through a tube at 550° C. The residence time in the reactor is 2.8 sec. After condensation, a mixture of 27.9% of acetic acid, 61.5% of dimethyl vinylphosphonate and 8.6% of starting compound is obtained. The selectivity is 97%.

EXAMPLE 4

In the vaporizer at 180° C., 134.1 g/h of dimethyl 2-acetoxyethanephosphonate and 14.9 g/h of methanol are vaporized at 30 mbar. The vapor is, together with 3.5 l/h (s.t.p.) of $N_2$, passed through a tube at 650° C. The residence time is 0.35 sec. After condensation, a mixture of 26.2% of acetic acid, 62.6% of dimethyl vinylphosphonate, 9.4% of methanol, 1.7% of methyl acetate and 0.1% of starting compound is obtained. The selectivity is over 99%.

We claim:

1. A process for preparing dimethyl vinylphosphonate by thermal dissociation of dimethyl 2-acetoxyethanephosphonate in the gas phase, which comprises vaporizing dimethyl 2-acetoxyethanephosphonate and dissociating it in a reaction zone without catalysis at temperatures of from 400° to 700° C. into dimethyl vinylphosphonate and acetic acid wherein the dissociation products are continuously removed from the reaction zone and wherein the residence time is from 0.05 to 3 seconds.

2. The process as claimed in claim 1, wherein the reaction is carried out at reduced pressure.

3. The process as claimed in claim 1, wherein the reaction is carried out at a pressure of above 500 mbar, with the difference between the total pressure and the partial pressure of the reaction components being produced by a gas which is inert under the reaction conditions.

4. The process as claimed in claim 1, wherein the reaction is carried out at a temperature of from 550° to 650° C.

5. The process as claimed in claim 1, wherein the residence time is from 0.3 to 3 seconds.

6. The process as claimed in claim 1, wherein from 1 to 100% by weight of methanol is added to the dimethyl 2-acetoxyethanephosphonate.

7. The process as claimed in claim 1, wherein the reaction is carried out at from 5 to 500 mbar.

8. The process as claimed in claim 1, wherein the reaction is carried out at from 10 to 50 mbar.

9. The process as claimed in claim 1, wherein from 5 to 20% by weight of methanol is added to the dimethyl 2-acetoxyethanephosphonate.

10. The process as claimed in claim 3, wherein the inert gas is $N_2$, He, Ar, $CO_2$ or the vapor of a lower hydrocarbon.

* * * * *